United States Patent [19]
Matson

[11] Patent Number: 4,511,659
[45] Date of Patent: Apr. 16, 1985

[54] LIQUID CHROMATOGRAPH WITH ELECTROCHEMICAL DETECTOR AND METHOD

[75] Inventor: Wayne R. Matson, Ayer, Mass.

[73] Assignee: ESA, Inc., Bedford, Mass.

[21] Appl. No.: 579,401

[22] Filed: Feb. 17, 1984

Related U.S. Application Data

[63] Continuation-in-part of Ser. No. 472,387, Mar. 4, 1983, abandoned, and a continuation-in-part of Ser. No. 425,183, Sep. 28, 1982, , which is a continuation of Ser. No. 111,917, Jan. 4, 1980, Pat. No. 4,404,065.

[51] Int. Cl.³ .................. G01N 27/52; G01N 33/48
[52] U.S. Cl. .................. 436/150; 73/61.1 C; 204/1 T; 204/403; 204/406; 204/411; 422/70; 436/111; 436/161; 436/175
[58] Field of Search .......... 436/68, 111, 150, 161, 436/175; 422/70; 204/403, 406, 411, 412, 1 K, 1 T; 73/61.1 C

[56] References Cited

U.S. PATENT DOCUMENTS 3,922,205 11/1975 McLean et al. .............. 204/1 T
4,233,031 11/1980 Matson et al. .............. 204/1 T X
4,338,811 7/1982 Miyagi et al. .............. 73/23.1
4,343,767 8/1982 Long et al. .............. 422/70

FOREIGN PATENT DOCUMENTS 51354 4/1980 Japan .............. 436/111

OTHER PUBLICATIONS

Aaron H. Anton et al., J. Pharmacol. Exp. Ther., 138, pp. 360-375, (1962).

Primary Examiner—G. L. Kaplan
Attorney, Agent, or Firm—Hayes Davis & Soloway

[57] ABSTRACT

An improved apparatus for electrochemically analyzing a sample in solution is described. The apparatus comprises an electrochemical detector comprising a plurality of electrochemically isolated flow cells arranged in series so as to define at least one flow path. Each of the electrochemical flow cells in turn comprises at least one working electrode, at least one reference electrode, and at least one counter electrode. Electrical potentials are applied to the various working electrodes so that the sample solution is cyclically subjected to oxidation and reduction conditions whereby selected substances contained in the sample solution may be electrically screened or modified prior to detection and measurement on a downstream sensing electrode.

26 Claims, 19 Drawing Figures

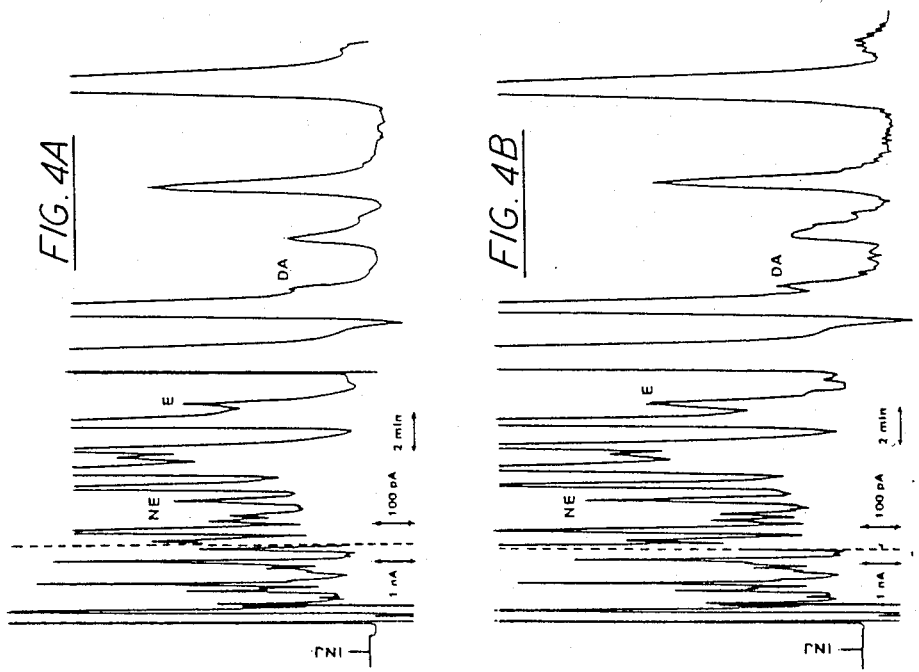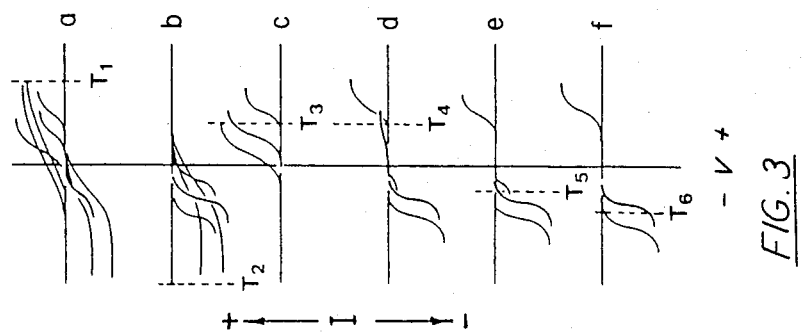

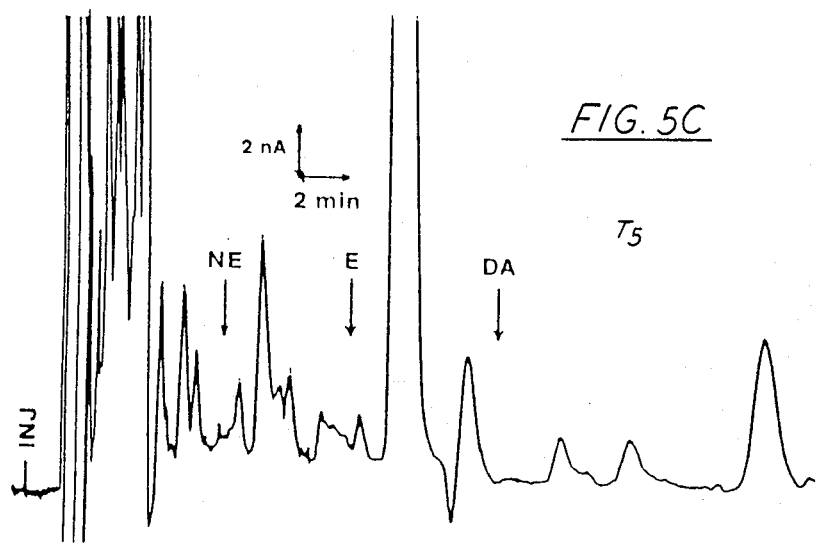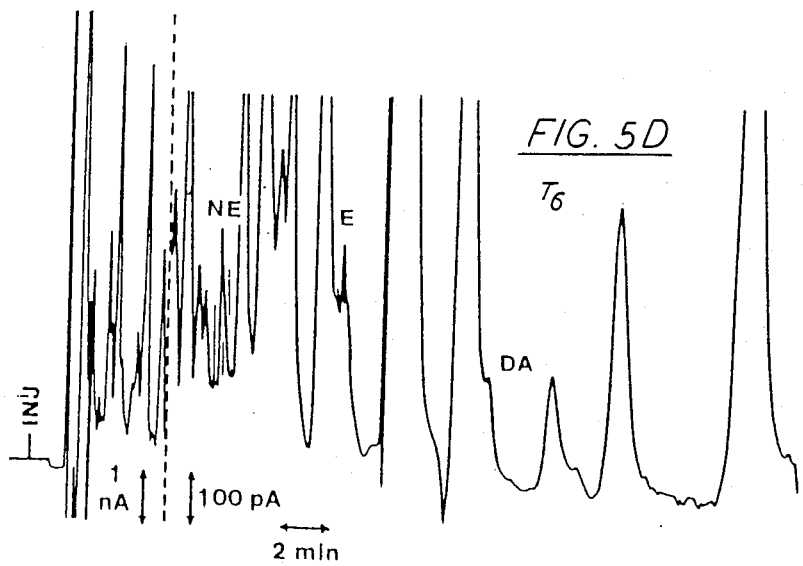

ARRAY CHROMATOGRAM
NORMAL CEREBROSPINAL FLUID (CSF)

COMPUTER PROCESSED DATA FROM ARRAY CHROMATOGRAMS

LIQUID CHROMATOGRAPH WITH ELECTROCHEMICAL DETECTOR AND METHOD

This application is in part a continuation of my co-pending application Ser. No. 472,387 filed Mar. 4, 1983 (now abandoned) and in part a continuation of my co-pending application Ser. No. 425,183 filed Sept. 28, 1982 which is, in turn, a continuation of my application Ser. No. 111,917 filed Jan. 4, 1980 (now U.S. Pat. No. 4,404,065).

This invention relates to electrochemical analytical systems for qualitatively and quantitatively testing electroactive materials in solution. The invention has particular utility for the detection and determination of electroactive organic substances such as catecholamines and their metabolites and will be described in connection with such utility although other uses are contemplated.

In recent years, LCEC (Liquid Chromatography with Electrochemical Detection) has become a common tool for the determination of catecholamines and their metabolites in biological fluids. Because of sensitivity limitations (typically 20–50 pg) and the complexity of biological samples, both separation and concentration steps typically have been necessary. Heretofore, plasma catecholamine analysis typically required three steps. First, the sample is collected and the catecholamines separated and concentrated, for example, using the alumina extraction procedure of Anton and Sayre (See A. H. Anton and D. F. Sayre, J. Pharmacol. Exp. Ther., 138 (1962), p. 360–375). The analytes, norepinephrine, epinephrine and dopamine, along with the internal standard DHBH (dihydroxybenzylamine), then are separated chromatographically, and finally detected electrochemically. Typical sample size requirements are 1.0 ml plasma or serum. In routine clinical use, there have been numerous problems with conventional techniques (alumina adsorption, ion exchange and extraction) due to a large number of poorly understood variables in the overall analysis system of sample acquisition, storage, preparation and sensor response. These problems have quite likely confused the relationships that may exist between levels and distribution of the catecholamines and various physiological and behavioral phenomena and disease states.

It is thus a primary object of the present invention to provide a novel and improved system, i.e., method and apparatus, which overcomes the aforesaid and other problems and limitations of the prior art.

Another primary object is to provide a novel and improved method and apparatus for analyzing a sample in order to qualitatively and/or quantitatively determine the presence of selected substances in the sample.

A more specific object of the present invention is to provide an electrochemical detection system of the aforesaid type which is capable of rapidly and reliably detecting and determining selected electroactive organic substances in biological samples.

In a preferred form of the invention it is used to detect an electrochemically reversible material, such as a catechol amine, in conjunction with a liquid chromatographic column which separates the constituents in time spaced relationships. In the analysis of complex biological materials such as blood serum and cerebrospinal fluids which may contain numerous different constituents, the important (e.g. abnormal) neurotransmitters to be identified may be present in only parts per trillion. While the chromatographic column can achieve macro separation of the various constituents it may not provide adequate spatial (in time) separation of the extremely small portion of neurotransmitters of interest from the much larger percentage of the many other fluids coeluted from the column at the same time as the neurotransmitter. Many of these interfering coeluted materials are electrochemically active but electrochemically irreversible while the neurotransmitters are both electrochemically active and electrochemically reversible.

In a preferred apparatus for practicing the invention, there is provided an electrochemical detection system comprising a plurality of coulometrically efficient electrochemical cells, in series, for sequentially oxidizing and reducing selected substances in a sample solution under controlled conditions prior to measurement on a downstream testing electrode or electrodes.

More specifically, in accordance with the present invention, a sample solution (e.g. a body fluid) is passed through a suitable chromatographic column and the eluant is streamed in contact with a series of electrochemically isolated, in-line coulometric electrodes operated under conditions so as to establish a series of "gates" for the sequential oxidation and reduction of substances in the sample solution whereby to screen (remove) selected interfering and electrochemically irreversible substances contained in the sample solution, while passing selected electrochemically reversible products for detection and measurement on a downstream electrode. The gate electrode series is followed in-line by one or more coulometric measuring electrodes for detecting and measuring the electrochemically reversible compounds of interest (e.g. neurotransmitters).

There are several beneficial effects of this approach to electrochemical analysis. Long-term drift in response is effectively eliminated by acquiring 100% of the signal. Poisoning of the electrode, a dominant problem with electrochemical sensors, is effectively eliminated by the use of a much larger relative surface area for reaction. The capability of analyzing 100% of a material allows the assay of compounds of unknown purity by relating them to the basic principles of electrochemical reaction embodied in Faraday's law. And, finally, and most important to the eventual development of array and gate cells, a coulometric electrode by virtue of its 100% efficiency allows sequential oxidation and/or reduction of compounds at successive in-line detectors.

The improved sensitivity of the detection system, particularly where two or more active testing electrodes follow the screening electrodes has given the ability to do direct injections of serum filtrates and has also allowed the generation of reproducible patterns of compounds with catecholamine like electrochemical behavior with up to 40 resolvable components. This provides the extremely interesting possibility of performing pattern recognition for the diagnosis or perhaps even predictive diagnosis, of various disorders or disease states.

Yet other objects of the invention will in part appear obvious and will in part appear hereinafter. The invention accordingly comprises the apparatus possessing the construction, combination of elements and arrangement of parts, and the process comprising the several steps and relation of one or more of such steps with respect to each of the others, all of which are exemplified in the following detailed description, and the scope of application as will be indicated in the claims.

For a fuller understanding of the nature and objects of the present invention, reference should be had to the following detailed description taken in combination with the accompanying drawings:

FIGS. 4A and 4B are chromatograms obtained in accordance with the present invention;

FIGS. 5A, 5B, 5C and 5D are a series of chromatograms obtained in accordance with the present invention;

The present invention provides an electrochemical detection apparatus capable of responding to and differentiating between electrochemically reversible species in a sample solution and for discriminating against species in a sample solution that are electrochemically irreversible. As applied to catecholamines, a sample solution containing catecholamines is flowed through a chromatographic column and the eluant is passed through a series of electrochemically isolated cells or "gates" operated at potentials resulting in sequential oxidation and reduction of various species contained in the sample solution. These gates are followed by one or more measuring electrodes for measuring electrochemical activity of compounds of interest. The strategy of analysis discriminates against both background current from the mobile phase itself and removes (screens) compounds that are irreversible, while the catecholamines are cycled back and forth from oxidized to reduced state at various potentials whereto to enhance the sensitivity and specificity of downstream detection and measuring electrodes.

For convenience of illustration the function of the gate cells is described as "removing" or "screening" the electrochemically irreversible compounds from the eluant. This is not what actually happens; these compounds are merely electrochemically altered by the gate cells so that the potential existing on the following detecting electrode(s) will not change the oxidation state of the "removed" compound and therefore the "removed" compound will not be detected and coulometrically measured. It is as if the "removed" compound were not present in the eluant. It is no longer electroactive under the detection conditions.

Further understanding of the features and objects of the present invention will be had from the following detailed description of one preferred embodiment of the invention which illustrates an electrochemical testing system for catecholamine analysis in blood. It will be understood, however, that the system of the present invention may be advantageously employed for detecting the presence of and measuring the concentration of various other electroactive substances in a sample solution.

Figure 1:
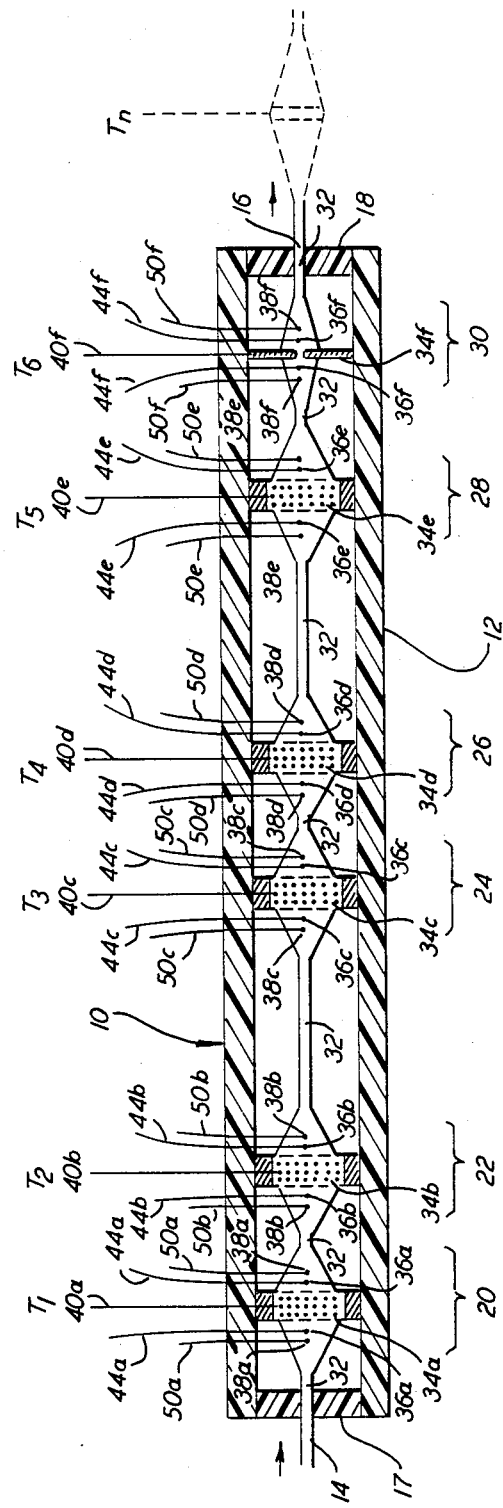
FIG. 1 is a side elevational view, in cross-section, of an electrochemical detection apparatus in accordance with the present invention.
Figure 2:
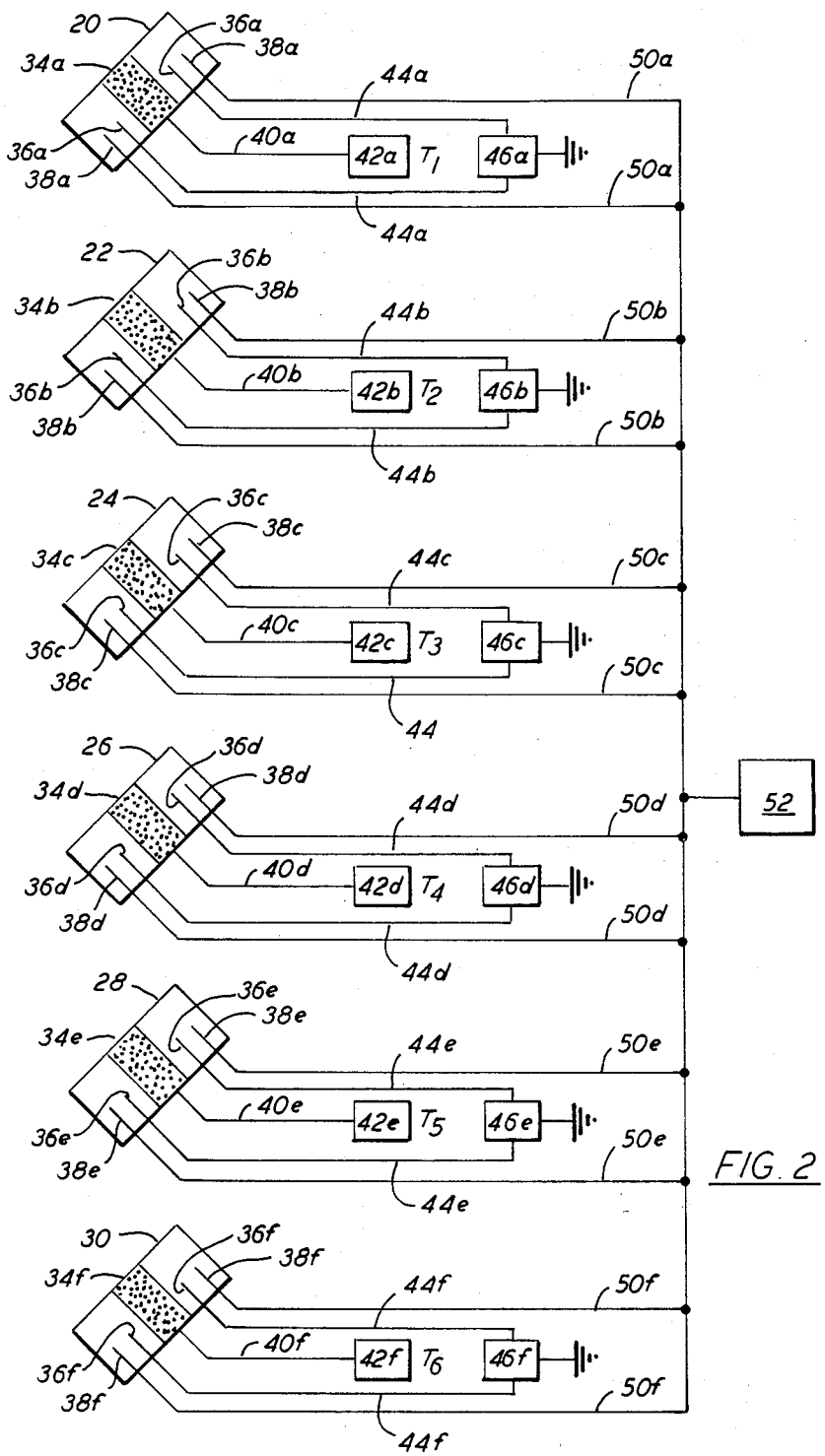
FIG. 2 is a block diagram of the electrical controls and functions of the electrochemical detection apparatus invention; and, FIG. 3 is a series of chart recordings showing the current in micro-amperes (MA) versus the potential in milli-volts (MV) typical of the electrochemically active species present in the fluids of the type which can be analyzed in accordance with the present invention.

The gate cell principle was evaluated using a cell configured typically as shown in FIGS. 1 and 2. In essence, a gate cell is designed to set up a unique window for a particular class of compounds (in the preferred embodiment, the three catecholamines—epinephrine, norepinephrine, and dopamine). FIG. 1 shows effectively a five-electrode gate cell with a measuring cell at the end of it. At the first electrode, all irreversible compounds outside the potential gate for catecholamines are oxidized and "removed". At the second electrode all irreversible reducible compounds outside of the potential gate for catecholamines are "removed". The third and fourth electrodes in this illustration are used as the equivalent of a single electrode to return the catecholamines to their oxidized state with as low a potential as possible to define a window which is specific for those catecholamines in the oxidative side of their C-V curve. The fifth element sets up a reduction gate for catecholamines, basically at the foot of the reduction wave, such that the measurement of the catecholamines at $T_6$ (at the sixth element) will be as specific as possible for that particular class of compounds.

Referring to the details of FIGS. 1 and 2, there is shown a preferred embodiment of the electrochemical detection apparatus of the present invention, indicated generally at 10. Electrochemical detection apparatus 10 comprises a hollow, liquid-tight enclosure indicated generally at 12 and having an inlet 14 and an outlet 16 found in a pair of end plates 17 and 18, respectively. Enclosure 12 is formed of a liquid-impervious, rigid, electrically insulating chemically inert material such as unplasticized polyvinylchloride, polytetraflouroethylene, flourohydrocarbon resin or the like. Disposed within enclosure 12 are six electrochemically isolated electrochemical cells 20, 22, 24, 26, 28 and 30. Electrochemical cells 20 . . . 30 are hydraulically connected to one another via stub tubing members 32 which together with cells 20 . . . 30 define a fluid flow path between inlet 14 and outlet 16. Each electrochemical cell 20 . . . 30 comprises a three electrode system consisting of at least one working electrode 34a, 34b, 34c, 34d, 34e and 34f, ($T_1 \ldots T_6$) respectively; at least one counter electrode 36a, 36b, 36c, 36d, 36e and 36f, respectively, and at least one reference electrode 38a, 38b, 38c, 38d, 38e and 38f, respectively. Electrochemical cells 20 . . . 30 are fixedly positioned within enclosure 12 by suitable means (not shown).

Each working electrode 34a . . . f ($T_1 \ldots T_6$) is in the form of a flat disc formed of a porous electrode base material such as fritted graphite or fritted carbon or other conductive fritted materials. Most of these preferably have a relatively large area to volume ratio to give large half times (up to 90) at the flow rates contemplated and with the electrochemically active materials of interest. Half time is the time required for half of a quantity of a compound to react at an electrode. Allowing a reaction to proceed for two half times causes 75% reaction, 5 half times 97%. Also provided are electrical connections 40a, 40b, 40c, 40d, 40e and 40f for connecting working electrodes 34a . . . f, ($T_1 \ldots T_6$) respectively, to potential controls 42a, 42b, 42c, 42d, 42e and 42f, respectively, for applying selected working potentials to the various working electrodes 34a . . . f; electrical connections 44a, 44b, 44c, 44d, 44e and 44f, respectively, to potential controls 46a, 46b, 46c, 46d, 46e and 46f, ($T_1 \ldots T_6$) respectively, for applying selected counter potentials to the various counter electrodes 36a . . . f; and, electrical connections 50a, 50b, 50c, 50d, 50e and 50f, respectively, for connecting reference electrodes 38a . . . f, respectively to a potential control 52 for applying a reference potential to the various reference electrodes 38a . . . f.

Counter electrodes 36a . . . f and reference electrodes 38a . . . f preferably comprise inert metal terminals such as platinum or palladium wire. Alternatively, reference electrodes 38a . . . f may comprise silver/silver chloride reference electrodes or the like. The counter electrodes 36a . . . f and reference electrodes 38a . . . f preferably are arranged in pairs to bracket an associated working electrode 34a . . . f.

As will become clear from the following description electrochemical cells 20, 22, 24, 26 and 28 act as gate electrodes for discriminating and screening interfering species, while electrochemical cell 30 contains the measuring electrode. In order to achieve high noise discrimination against pressure spikes and voltage fluctuations the measuring electrode should have a relatively small electrode area and thus a relatively small number (e.g. 4) of reaction half-times as compared with the various upstream gate electrodes.

Further understanding of the principles and advantages of the present invention may be had by reference to the following examples which are based upon electrochemical analysis employing an electrochemical apparatus made in accordance with FIGS. 1 and 2 and comprising six electrochemically isolated electrochemical cells 20 . . . 30. The working electrodes 34a . . . e each comprise fritted graphite discs each having a working area of approximately 4 cm² (90 half times). Electrode 34f has a working area of approximately 0.3 cm² (4 half times). Counter electrodes 36a . . . f and reference electrodes 38a . . . f comprise inert metal terminals.

EXAMPLE I

The purpose of this example is to show how the electrochemical apparatus of the present invention can achieve quantitation of catecholamines in a direct serum filtrate, i.e., without any sample pretreatment. As a preliminary test of the apparatus for serum filtrates, a "mock" serum sample was prepared by adding 100 picograms (10 microliters of $10^{-8}$ g/ml) of epinephrin, norepinephrin and dopamine to mock inorganic serum.

The sample solution was flowed through a 25,000 Molecular Weight cut off filter and the filtrate was injected onto a Brownlee 22 cm Rp 18 5 liquid chromatography column and flowed through the electrochemical apparatus described. The Electrochemical Detection parameters were:

| Working Electrode | Voltage (in millivolts) | Full Scale Response | Comment |
|---|---|---|---|
| 34a ($T_1$) | +300 | 200 na | (99.9% + oxidation) |
| 34b ($T_2$) | −350 |  | (99.9% + reduction) |
| 34c ($T_3$) | +200 | 200 na | (80% oxidation) |
| 34d ($T_4$) | +200 |  | (80% oxidation) |
| 34e ($T_5$) | −60 | 20 na | (10% reduction) |
| 34f ($T_6$) | −240 volts | 1 na | (90% reduction) |

Recoveries in the filtrates were 100± 2% for epinephrin, norepinephrin and dopamine. Thus epinephrine, norepinephrine and dopamine proceeded through the system unchanged.

In the sequential oxidation and reduction of norepinephrine, epinephrine and dopamine, the important thing to notice in this example is that the reduction and the oxidation are both 100% coulometrically efficient. If another oxidation electrode and another reduction electrode in series after this pair of electrodes were set up, there would be effectively no decrease in the signal. The concept of multiple electrodes taking a compound through a series of oxidation and reduction steps with no loss of signal permits extending the process to the production of a "gate" cell with a number of different oxidation/reduction electrode steps specific for particular classes of compounds.

FIG. 3A shows a schematic representation of a possible group of C-V curves of reversible and irreversible substances presented to the sensor chain at $T_1$.

FIG. 3B shows the C-V curves of the compounds presented to $T_2$, after $T_1$ has oxidized the irreversible compounds and converted the reversible ones to the oxidized form. Note here that $T_1$ is kept at the smallest possible potential, consistent with 99+% oxidation, to prevent other compounds from going into the oxidized form since the final analysis is to be done in the reduction mode.

FIG. 3C shows the C-V curves presented to $T_3$. The reversible compounds have been returned to the reduced form. Any irreversible reducible materials have been eliminated by setting $T_2$ 110 mv more negative than $T_6$.

FIGS. 3D and 3E show the C-V curves presented to $T_4$ after $T_3$ oxidation and to $T_5$ after $T_4$ oxidation. $T_3$ and $T_4$ electrodes are set at the 80% level of the catecholamine waves such that they will return approximately 96% of the catecholamines to the oxidized state without returning a significant quantity of compounds with a higher oxidation potential.

FIG. 3F shows the C-V curves presented to $T_6$ after screening by $T_5$.

While the invention has been described as involving a gate array in which the sequence of steps has been reduction, oxidation and reduction (for test) other sequences can be equally used. For example the gates may first oxidize and then reduce with subsequent detection in the oxidative mode.

The increased sensitivity and selectivity of the six electrode system offer several approaches to the problems in catecholamine analysis and speciation. The ability to quantitate 1–5 pg levels offers the possibility of performing a blood, serum or plasma analysis on micro samples (fingerstick or earstick) to avoid the catecholamine elevation associated with the trauma of a venapuncture sample.

EXAMPLE II

Aliquots of 300 microliter of serum were taken through an Amicon 25000 MW cutoff filter by centrifugation at 1000 xg for 25 minutes, yielding approximately 115 microliters of filtrate. Aliquots of serum spiked at 100 picograms per milliliter with epinhephrine, norepinephrine and dompamine were similarly prepared as controls. Prepared aliquots were flowed through the chromatography column and electrochemical apparatus as in Example I. The required electrical potentials are the same as employed in studies of mock inorganic serum and the results at the 6th electrode 34F ($T_6$) recorded at FIG. 4A and B, where 4A is the unspiked serum and 4B is the serum spiked to 100 pg/ml.

The selectivity of the system can be shown by considering sequential chromatograms shown in FIG. 5 as they relate to the voltammograms in FIGS. 3A–F.

Figure 5A:
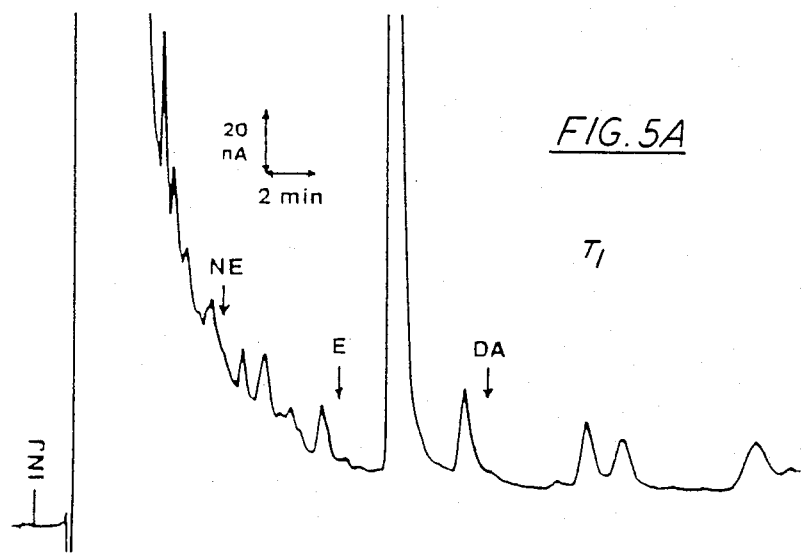

FIG. 5A shows the chromatogram (obtained by plotting the current output) at electrode $34a$ ($T_1$). It should be related to the voltammagram in FIG. 3A.

Figure 5B:
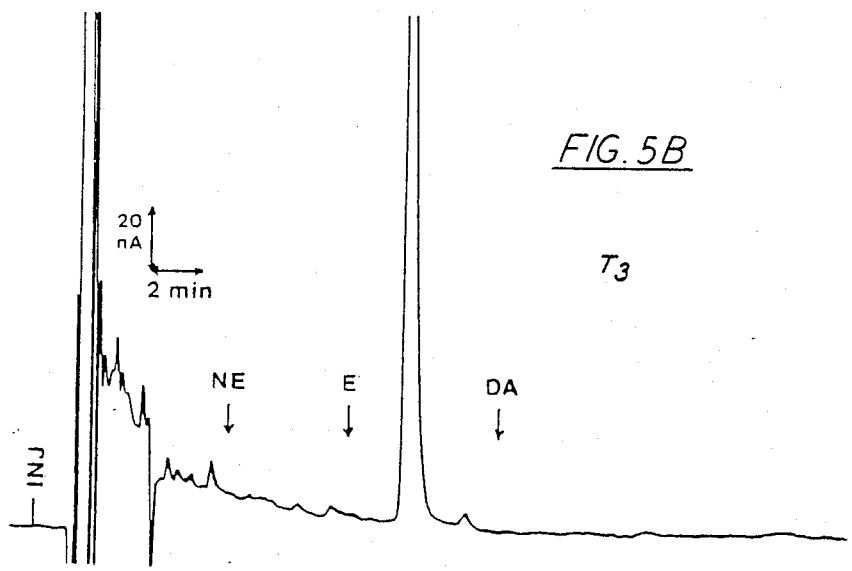

FIG. 5B shows the chromatogram (obtained by plotting the current output) at electrode $34c$ ($T_3$). It should be related to the voltammagram in FIG. 3C;

FIG. 5C shows the chromatogram (obtained by plotting the current output) at electrode $34e$ ($T_5$). It should be related to the voltammagram on FIG. 3E; and FIG. 5D shows the chromatogram (obtained by plotting the current output at electrode $34f$ ($T_6$) after electrode $34e$ reduction. It should be related to the voltammagram in FIG. 3F.

As can be seen there results a high degree of signal separation.

The chromatogram at $T_1$ should be compared to the chromatogram at $T_6$ shown in FIG. 5D after the gate cells have eliminated those compounds which do not follow the oxidation/reduction pattern of the catecholamines. It can be seen that the compounds which presented themselves as only a smear after the void volume in $T_1$ are now resolved in the void volume into a series of discrete and measurable peaks. The norepinephrine, epinephrine and dopamine shown here at 200 times the sensitivity achieved at $T_1$, are resolved and measurable. The norepinephrine is fully resolved and the epinephrine and dopamine are resolved as shoulders on co-eluting peaks. While this technique does not yield completely clean signals for the catecholamines, it is approximately 10,000 times more capable of resolving these materials than the single electrode technique. In other words, the gate cells give approximately $10^3$ or $10^4$ resolution for the catecholamines over the other components which are seen in serum in this particular use.

High selectivity offers the possibility of investigating binding of catecholamines to both large and small protein or other macromolecular materials which may be a factor in their biochemical activity. Samples of serum ultrafiltrates for instance, can be directly injected on column, and the catecholamine moieties determined. It should be noted that direct serum injections can also be made, except that after only 3–4 injections the guard cartridge column must be changed because of pressure buildup from protein precipitates.

The feasibility of these approaches was tested in a series of preliminary experiments.

EXAMPLE III

The purpose of this example is to show the use of the electrochemical testing system of the present invention for catecholamine analysis of blood.

Figure 6:
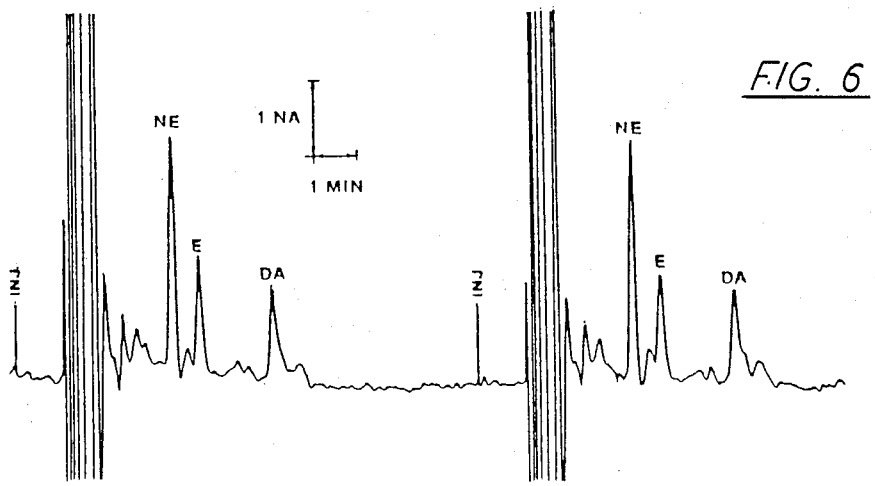
FIG. 6 is a set of duplicate chromatograms obtained in accordance with the present invention.

Sample Preparation:

A sample solution was prepared by adding the contents of a 100 microliter (EDTA anticoagulated blood) capillary to 200 microliters of a 2M $NH_4OH$—$NH_4Cl$ pH 8.5 buffer containing 0.2% W/V diphenyl borate ethanolamine and 0.2% W/V EDTA. Two aliquots of 500 microliters of n-hexane and 1% W/V n-octanol containing 0.25% W/V tetraoctylammonium bromide were added, shaken for two minutes and removed (450 microliters of the first aliquot and 500 microliters of the second aliquot were taken and transferred to a conical tube). 500 microliters of octanol and 110 microliters of 0.08 M acetic acid were added, the tube shaken for two minutes, centrifuged for five minutes, and 100 $\mu$l of the 0.08 acetic acid solution was flowed through the chromatography column and electrochemical apparatus as in Example I. Results were recorded shown in FIG. 6 for duplicate samples.

As will be clear from the foregoing taking the catecholamines back and forth from oxidized to reduced state makes the analysis independent of the state of oxidation of the catecholamines in the sample, thus reducing the problem of sample stabilization. Also, the high selectivity and sensitivity of the analysis permit using catecholamines as a screening test in large-scale populations where central nervous system damage is suspected (e.g., lead poisoning, dioxin exposure, agent orange exposure, pesticide exposure, etc.). High selectivity also permits the investigation of the binding of catecholamines to both large and small protein or other macromolecular materials which may be a factor in their biochemical activity.

One skilled in the art will recognize the aforesaid invention is susceptible to modification. Thus, for example, while the electrochemical apparatus has been illustrated as having five electrochemically isolated gate cells, any number of electrochemically isolated electrochemical-gate cells may be employed in series to achieve the desired results. Moreover, reaction half-times may be modified by manipulating individual cell volumes which in turn may reduce certain kinds of noise. Also, two or more sensing electrode cells may be employed downstream of one another to detect and measure additional groups of compounds of interest. For example, after a four-electrode gate sequence to eliminate irreversible substances and define the upper and lower potential limits, a sequence of sensors (for example 10 to 16), if desired, including also additional gate electrodes, could be arranged in an increasing oxidative and then reductive modes. This will effectively display the current voltage curves for eluting compounds for both their oxidative and reductive modes. The current from each electrode will produce one set of simultaneous equations as follows:

$$i = A(C_a) + B(C_b) + C(C_c). \qquad \text{I.}$$

where A, B and C are constants defined by the potential and the nature of the compounds a, b and c and where $C_a$, $C_b$, $C_c$, ... are the concentrations of a, b and c. It would then be possible to solve and display, for as many coeluting components as there are sensors in the array, providing that there is not an absolute identify in the signature or current voltage curve. Employing a plurality of sensors in sequence would enhance sensitivity of the cells, and also enhance separation of compounds that coelute.

EXAMPLE IV

In this situation the equipment of FIG. 1 was modified by adding a second detector cell (see dotted line $T_n$) down stream of detector cell 30. This second detector cell $T_n$ was identical to cell 30 but was operated at a voltage ($T_n$) of $-260$ mv and ($T_6$) was operated at $-160$ mv rather than $-240$ mv of Example I to III at cell 30. $T_6$ and $T_n$ fed to CPU (see FIG. 7). In this FIG. 7 in this example the sample to be tested was human cerebrospinal fluid.

The resulting signals from the two detector electrodes were compared in a central processing unit (see FIG. 7) and by dividing the more positive signal by the more negative signal one is able to obtain a peaked "signature" corresponding to each neurotransmitter in the sample. When these signatures are compared to peak signatures for standard chromatographs made from normal neurotransmitters one can (a) identify each neurotransmitter and (b) identify those neurotransmitters having abnormalities of response to the system.

Figure 7:
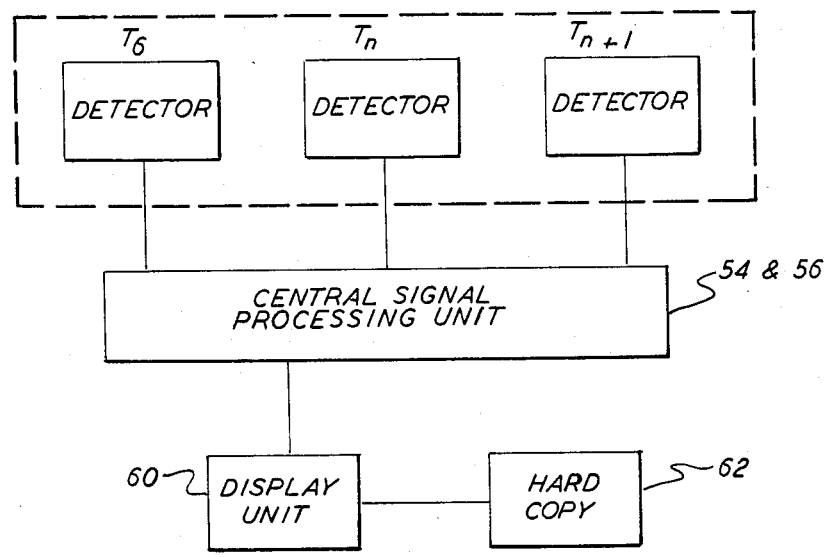
FIG. 7 is a schematic diagrammatic drawing of a detection system according to the present invention wherein a plurality of test (or measuring) cells are employed after the gate cells and the outputs of the test cells are processed by a central processing unit.
Figure 7A:
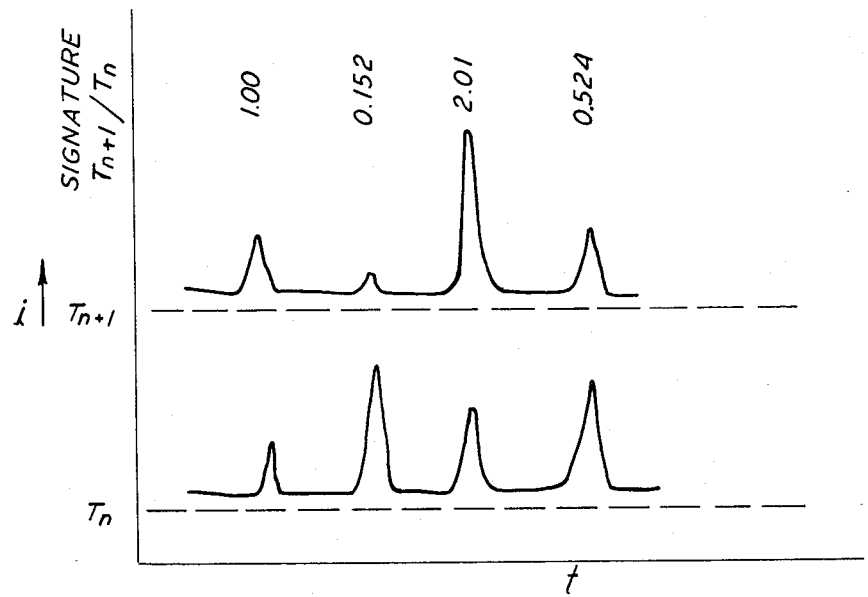
FIG. 7A is representative of one type of output from the system of FIG. 7.

FIG. 7 is a block diagram of a system for processing such dual signals and FIG. 7A shows a print out (from the computer) of the signal resulting from dividing the signal from cell 30 ($T_6$) by the signal from the second cell ($T_n$). The elements illustrated in FIG. 7 are given the same numbers as the equivalent elements in FIGS. 8 and 9.

Through the use of peak signatures, there have been detected in the analysis of CSF and brain tissue several peaks whose "signatures" were clearly *not* identical to that of the standard compound normally observed at that retention time. The previous method would not have allowed for the detection of this co-eluting compound and would have resulted in erroneous data. This new technology has clearly provided a much needed method for determining the existence of co-eluting compounds and has virtually eliminated the misidentification of neurotransmitters.

Additionally, two-dimensional pattern diagrams, i.e., electrochemical fingerprints of various selected materials, can be generated, similar to two-dimensional pattern diagrams achieved by standard chromatography techniques by suitably integrating signals on various electrodes. In such case, samples of known substances may be flowed through the electrochemical apparatus, and two-dimensional pattern diagrams in the form of voltammograms representing the selected substances generated using the apparatus and procedures above described. The resulting pattern diagrams may be stored in a suitable central processing unit for subsequent pattern matching and identification.

Figure 8:
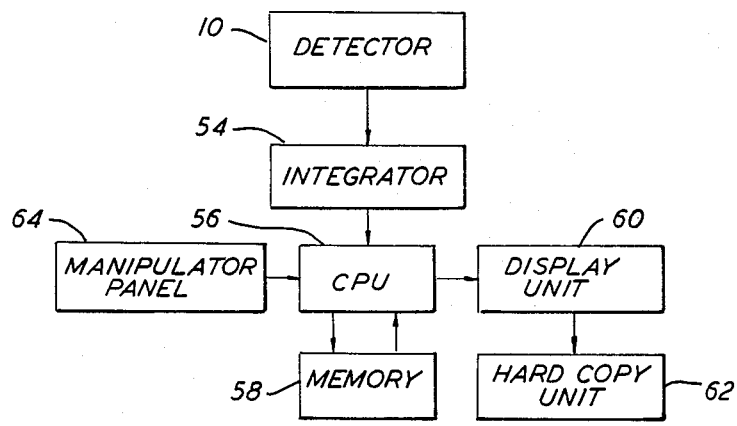
FIG. 8 is a flow chart of an embodiment of disease and detection diagnostic method according to the present invention.
Figure 9:
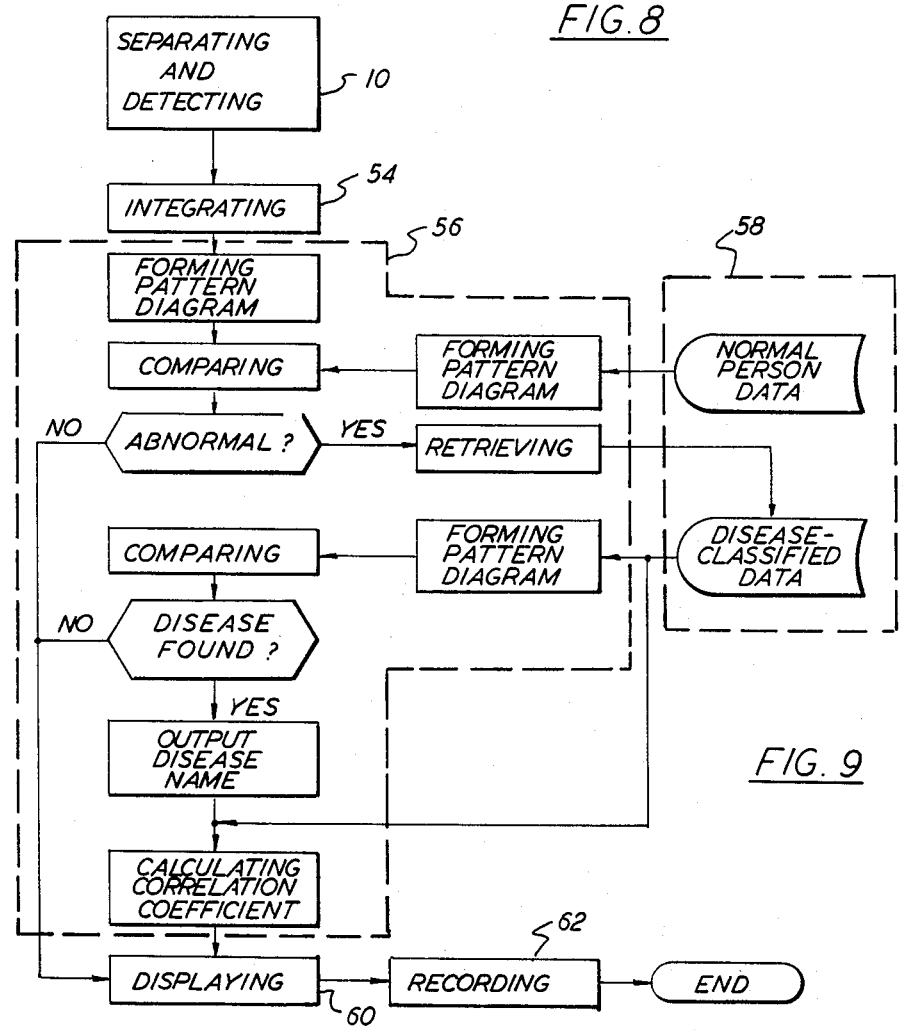
FIG. 9 is a block diagram of an electrochemical detection and diagnostic apparatus according to the present invention and adapted for the practice of the method shown in FIG. 8.

The apparatus and process thus described also may be advantageously employed for directly analyzing body fluids such as urine or blood for the purpose of diagnosing diseases of a subject, thus providing marked improvements over the many step chromatographic analysis techniques reported by A. B. Robinson and L. Cauling, in the paper entitled "Techniques of Ortho-Molecular Diagnosis" in *Clinical Chemistry*, Vol. 20, No. 8, 1974, pages 967–965, and by Miyagi et al, in U.S. Pat. No. 4,338,811. Referring to FIGS. 8 and 9, a sample fluid may be directly streamed into the electrochemical detection apparatus 10 as described in detail supra, where substances of interest may be separated and detected in the manner previously described. Individual peaks in the output signal from the detector 10 may then be integrated in an integrator 54, and the output signal from the integrator 54 applied to a central processing unit 56 which is referred to as a CPU hereinafter as described by Myagacuate. In the CPU 56, a two-dimensional pattern diagram representing the relation between the peak areas and the retention times provided by the input signal is formed according to a preset program. When peak matching (shown in FIG. 8) is required, a reference chromatogram is read out from a memory 58 such as a magnetic tape or a magnetic disk, and the two dimensional pattern diagram above described is formed after the CPU 56 judges whether or not the retention time of each peak in the subject's chromatogram coincides with the retention time of the corresponding peak in the reference chromatogram and carries out peak matching when coincidence is not detected.

Then, the data of the upper and lower limits of normal persons are read out from the memory 58 upper limit pattern diagram and lower limit pattern diagram of the normal persons in the CPU 56. The pattern diagram of the data of the subject is then compared geographically with these upper and lower limit pattern diagrams in the CPU 56 so as to judge whether the subject is normal or abnormal. The result of judgment is displayed on a display unit 60 and recorded by a hard copy unit 62. As described hereinbefore, the process of the comparison and judgment may be displayed when so desired.

As shown in FIG. 9, the process of disease diagnosis is completed when the subject is judged to be normal. When, on the other hand, the subject is judged to be abnormal, the CPU 56 retrieves disease data in a manner as described hereinbefore from the file of classified diseases stored in the memory 58. On the basis of the thus retrieved disease data, the CPU 56 forms the upper limit pattern diagram and lower limit pattern diagram of the disease and compares geographically these pattern diagrams with the subject's pattern diagram so as to select the corresponding disease or analogous disease. Further the CPU 56 calculates the correlation coefficient between the pattern diagram of the subject and the average-valve curve of the selected disease. The result of selection of the corresponding disease or analogous disease, the result of calculation of the correlation coefficient and/or the process of disease diagnosis by comparison of the pattern diagrams, when so desired, are displayed on the display unit 60 and recorded by the hard copy unit 62. When it is necessary to modify some of the data on the basis of doctor's other observations in the course of judgment of the normality or abnormality or in the course of disease selection, necessary data are applied from a manipulator panel 64 to the CPU 56 for the purpose of modification of the data.

As mentioned previously, more than two working or test electrodes can be employed in the device of FIGS. 1 and 2. Such a cell is, for convenience, called an array cell.

To lead into the concept of an array cell, consider the chromatographic pattern which is seen at $T_5$, in FIG. 5C. Many of the peaks seen at $T_6$ (FIG. 5D) are displayed with various magnitudes on $T_5$. The concept of an array cell is basically that if there were a number of cells following the gate cell, whose potentials were arrayed in equal potential increments, for instance between −60 and −300 millivolts, those compounds which are shown here as co-eluting peaks on a time axis would be separated by their appearance across the array on the voltage axis.

In order to explain this concept more fully, it is useful to look at the basic concept of an array cell or the concept of displaying a chromatogram across a voltage axis as well as a time axis during a chromatographic separation.

Figure 10:
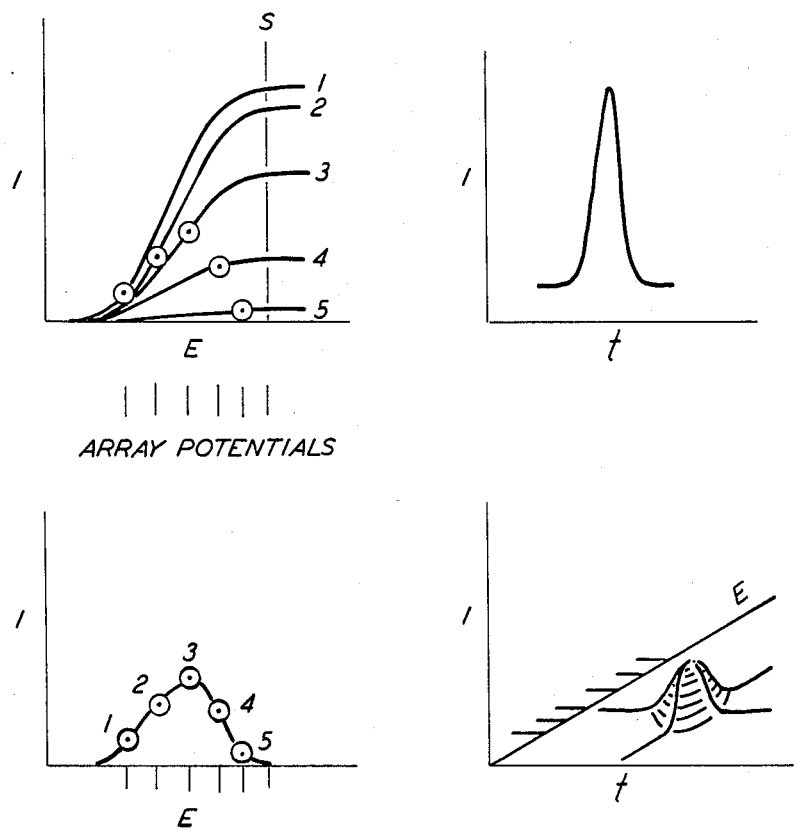
FIG. 10 is a series of graphs showing the effect of analyzing a single electrochemically active species at a series of different potentials.
Figure 11:
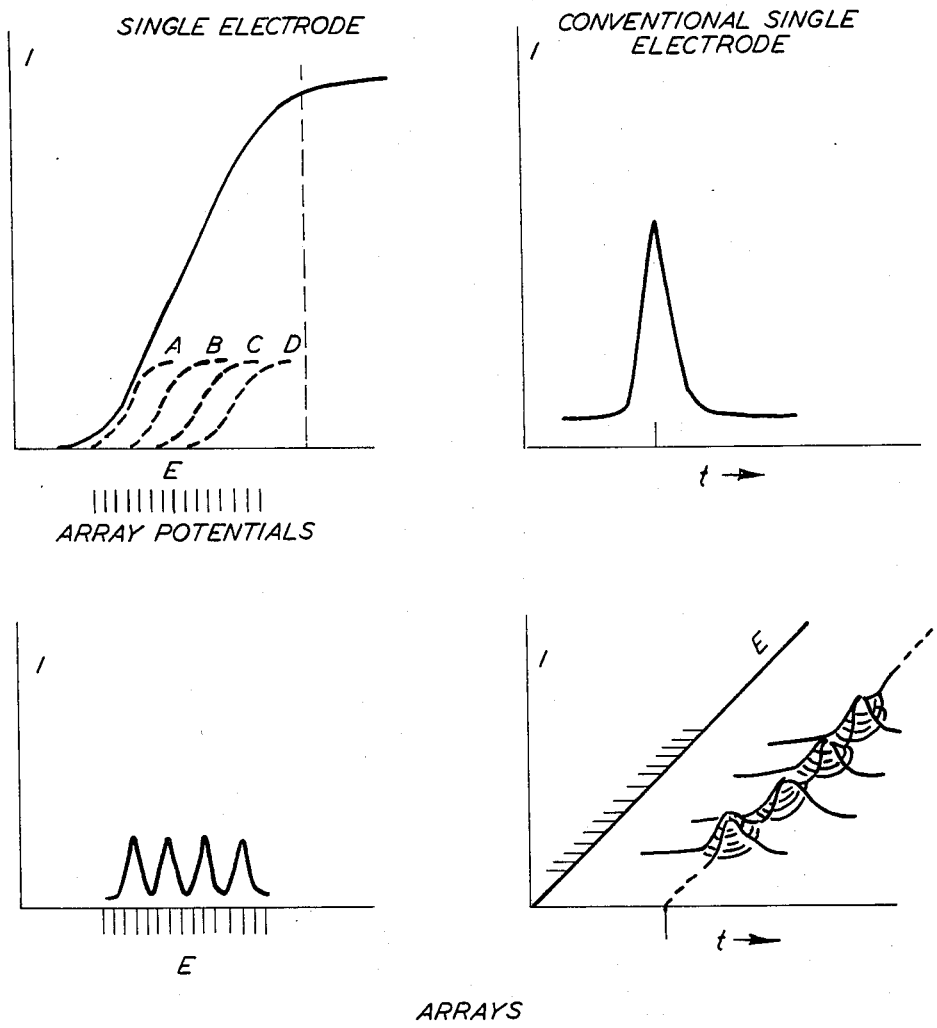
FIG. 11 is a series of graphs showing the effect of analyzing a plurality of coeluting electrochemically active species at a series of different potentials.

FIG. 10 describes the concept of a C-V curve to show how an array cell with potentials incremented across a voltage axis would act to convert it into a peak across that voltage axis.

As the material whose C-V curve is represented by the top line (1) in the upper left figure is presented to the first element in the array, a certain amount of that material will be used up, giving a signal shown at the first point in the bottom left drawing. A diminished concentration of the material of interest (line 2) will then be presented to the second element in the array, which will then react at the second sensor potential to give a signal shown by the magnitude of the second point. A further diminished amount of material (line 3) is presented to the third element of the array and then reacts, giving a signal shown at the peak of the array. Finally, the further diminished concentration of the material will be presented to the fourth element of the array which will take basically all that is left, causing the signal to fall off of the peak. The sixth element and the fifth element of the array will have nothing left to see and will resolve again to baseline. Chromatographically, the first case of a current-voltage curve with an electrode set at the top of the wave would show a peak resolving itself in time at the upper right. The second instance where an array provides a voltage axis would show a peak resolving itself in the voltage axis. The array cell chromatogram shown in the lower right gives both peak potential and peak time for the compound, instead of only a peak time.

Figure 12:
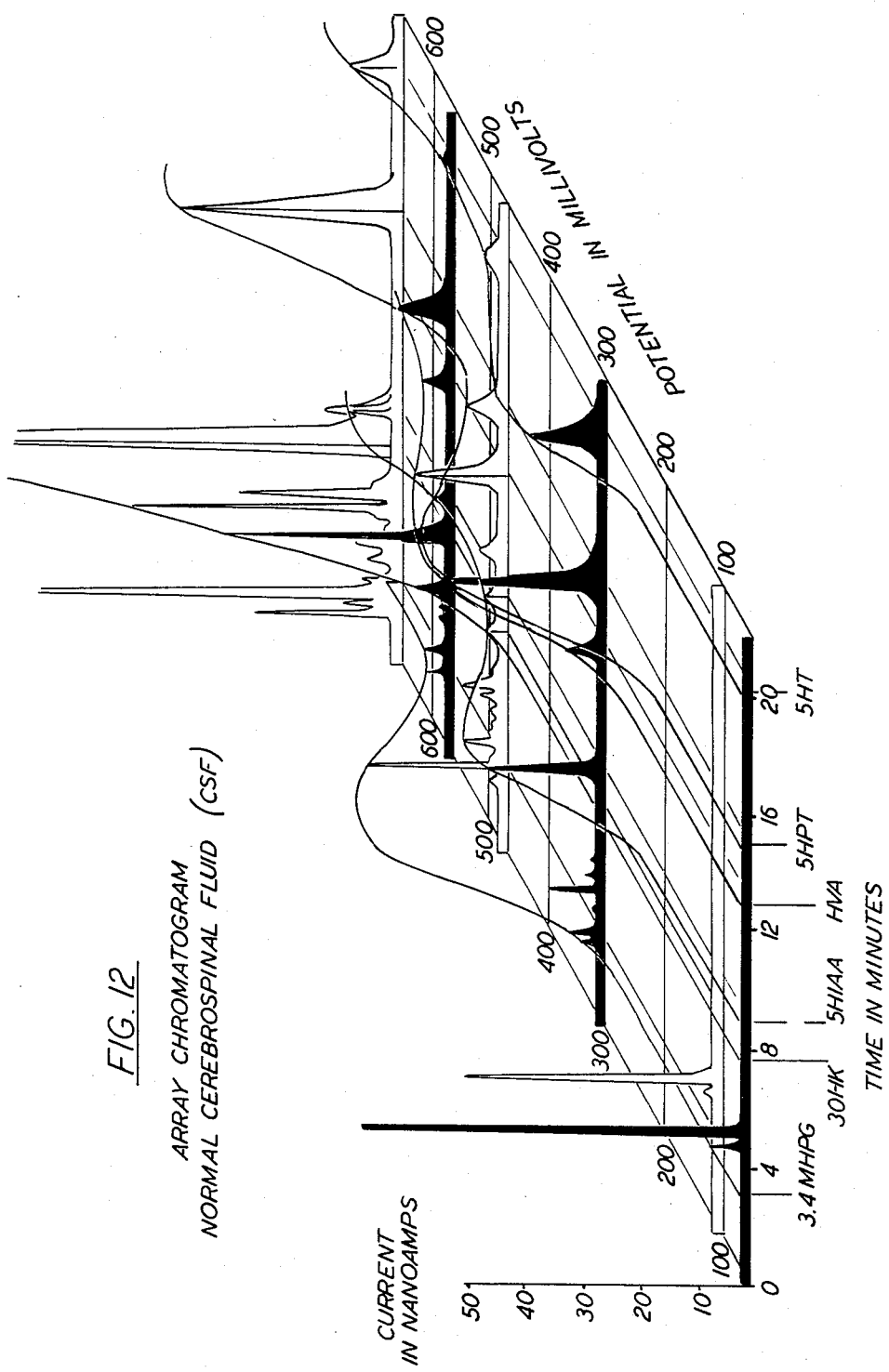
FIG. 12 is an array chromatogram of normal cerebrospinal fluid wherein a plurality of array cells are employed.

The effectiveness of this procedure in increasing the separability and resolution of compounds can be seen in FIG. 12 illustrating the array cell separation of four co-eluting peaks (A, B, C, and D) with current-voltage curves shown as dotted lines at the top left. In a simple single-electrode case, all of the current-voltage curves would combine into a single current-voltage curve shown as the upper line in the top left. A chromatogram from a single electrode placed at the potential shown would resolve in time alone as only a single peak. However, if an array of elements is placed across the region of the voltage curve (as shown in the middle left), each of these current-voltage curves will resolve itself into a peak at a particular voltage in the array, as shown in the lower left. If the chromatogram from the array cell is plotted with a voltage axis added, these peaks would resolve across the voltage axis into four separate hills or four separate peaks as shown in the lower right. In the time axis, however, they would still be only a single peak. In practice, it has been possible to resolve co-eluting peaks with C-V curves differing by 30 to 40 millivolts. Thus over a voltage range of 0 to 600 millivolts, the resolving power (or the number of compounds that can be detected) in a particular chromatogram is increased by up to a factor of 20. It should be noted that the eluant will pass each measuring electrode in sequence, giving some small time spacing between the signals from the sequential electrodes. However, because of the relatively small volume of the electrodes, the time interval between sequential electrodes in-series under normal chromatographic conditions can be held to approximately fifty msec. This allows up to twenty electrodes to be placed in series with a one second delay from the first electrode to the twentieth. This is an insignificant time with respect to the time of elution of peak in the chromatogram. Furthermore, since the time lag is constant, it can be corrected in the CPU 56 FIG. 8 such that chromatograms from each electrode display simultaneously for a given compound. Accordingly the voltage separated signals appear to occur at essentially the same time for each component.

A six detector embodiment of FIG. 1 using the array cell concept has been used in some initial studies of cerebrospinal fluid from patients with dementia of the Alzheimer type and from normals. The preliminary study focused on three areas: first, conditions under which the maximum amount of information from the array cell could be obtained; second, studies under normal chromatographic conditions using the array cell to look for co-eluting peaks that could have caused interferences with values reported previously in the literature for certain of the neurotransmitters and metabolites; and third, and perhaps most important, utilizing the array cells to search for binary differences between CSF of normals and patients with dementia of the Alzheimer type. Because the limited number of samples available were not felt to be adequate to show any significant differences simply in the relative levels or ratios of the dominant neurotransmitters and their metabolites, initial efforts focused on binary differences.

In the first study in which the array cell assembly was run at different gains and across different voltage regions of the chromatogram with a narrow potential gap across the array, it was possible to resolve approximately 100 separate components from samples of cerebrospinal fluid.

In the second study, using normal chromatographic conditions which have been reported previously in the literature, in approximately 15% of the cases there would have been interferences for certain of the dominant neurotransmitters and their matabolites which without the array cell technology would have gone undetected and unreported.

In the third study, where the majority of effort was placed, one significant binary difference between samples from patients with dementia of the Alzheimer type and normals was found in the apparent oxidation states of the neurotransmitters serotonin or 5-hydroxy tryptamine (5 HT), and its precursor 5-hydroxy tryptophan (5 HTP). This finding is of some interest technologically because it would have been impossible to discern with any other detection scheme than the use of an array cell which is capable of presenting the entire current-voltage curve for a particular compound.

FIG. 12 shows the representation of six simultaneously occurring chromatograms at each of the 6 elements of a six-sensor array for a normal sample of cerebrospinal fluid (20 microliters injected under typical chromatographic condition). Each of these chromatograms is displayed on a time axis (horizontal), and on a voltage axis (45° line) at the particular potential where the sensor was held during the chromatography. In this system the gate cells are arranged to remove the electrochemically irreversible compounds and the detector cells are operated in the oxidative mode, the gate cells having put the electrochemically reversible materials in the fully reduced state. Thus for sensor one at +50 millivolts, there is a chromatogram along the 50 millivolt line on the voltage axis. For sensor three at +300 millivolts, there is a chromatogram along the +300 mv line. A peak eluting from the chromatograph (for instance the first one outlined with a curved line across the voltage axis for 3,4-MHPG) will display across the voltage axis, following the curved line which is drawn in from the current-voltage characteristics of the 3,4-MHPG. For 5-hydroxy indoleacetic acid, the third curved line across the voltage axis shows the first oxidation of the 5-hydroxy indoleacetic acid followed by a second oxidation step.

The compound serotonin and its precursor, 5-hydroxy tryptophan, also oxidize in two discrete steps. The first step is the oxidation of the hydroxyl on the benzene ring followed by the oxidation of the nitrogen in the indole ring at a higher potential. Using an array cell, the two oxidations display as two distinct peaks as a function of increasing voltage in the array as shown by the fifth curved line across the array for the 5-hydroxy tryptophan and the sixth curved line for serotonin.

In all of the normals investigated, the 5-hydroxy tryptophan and the serotonin (5-hydroxy tryptamine), displayed a characteristic voltage signature for the fully reduced state of the compound, that is to say they displayed a peak on the third sensor and a peak on the sixth sensor with a low signal on the fourth and fifth sensors.

Figure 13:
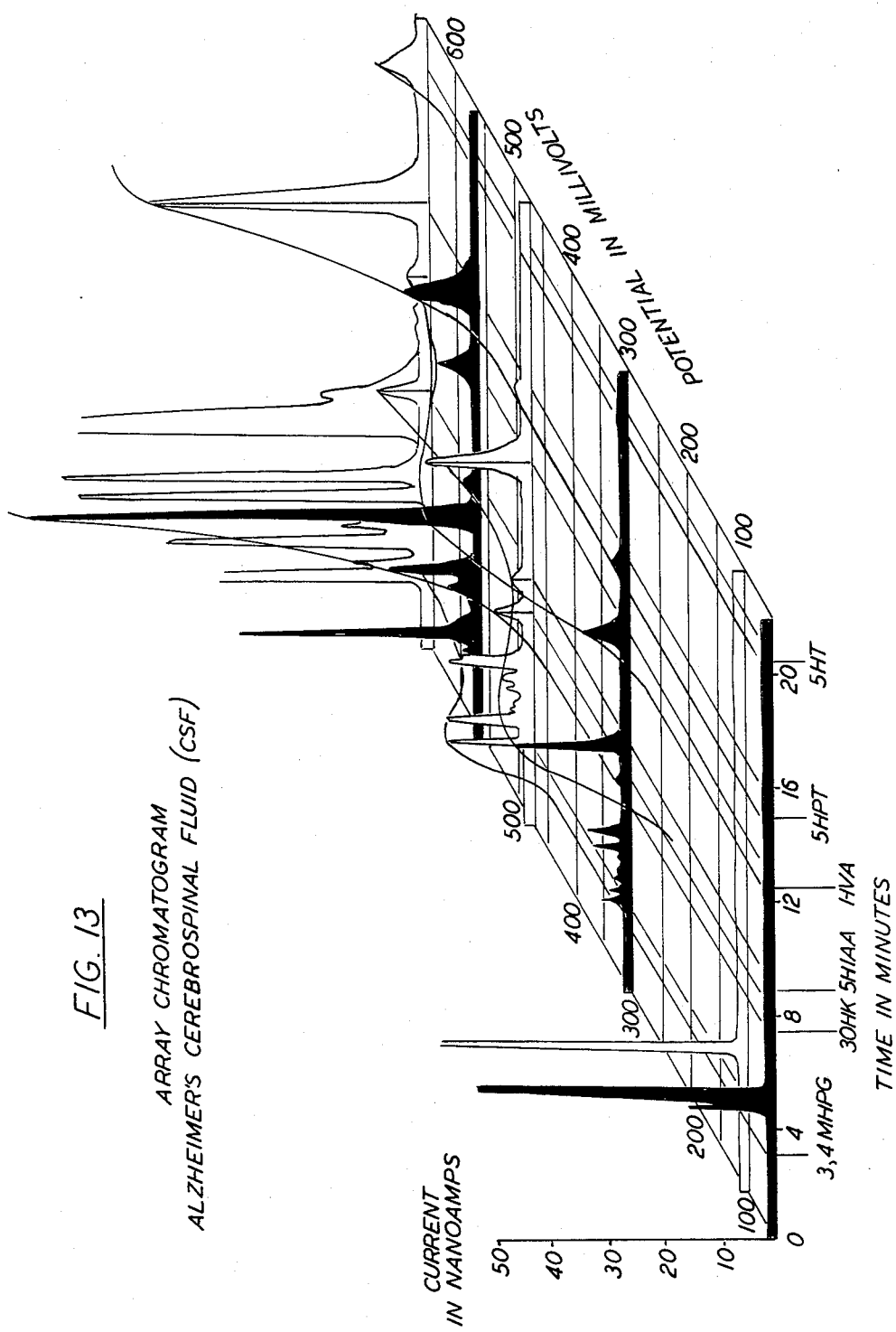
FIG. 13 is similar to FIG. 12 but is for an Alzheimer's cerebrospinal fluid.

In the array chromatograms of CSF samples from patients with dementia of the Alzheimer type, an example of which is shown in FIG. 13, the 5-hydroxy tryptamine and the 5-hydroxy tryptophan displayed only the peaks on the sixth electrode and a small peak on the fifth. The initial indication of this data is that in the Alzheimer's samples serotonin and its precursor exist in a partially oxidized form. The implications of this are unknown. It is possible that this may be an effect from metal complexation with the indoles (which may tie in with elevated aluminum levels) in which the bound metal ion withdraws electrons from the hydroquinone moiety. It may indicate a different enzymatic pathway or deficiency. The effect may also be a sample-related anomaly. However, it should be pointed out that at least in this instance; it is the unique capability of the technology that allows the observation of this effect.

The display of this data as a series of curves along a voltage and time axis is somewhat difficult to read. Consequently, in a preliminary fashion to improve the data readout, current-voltage algorithms for the eluting compounds have been applied across the voltage axis to locate them at a point in the voltage and time axis of the chromatogram. They can then be displayed at this point as a line representative of the total quantity of the material eluting.

Figure 14:
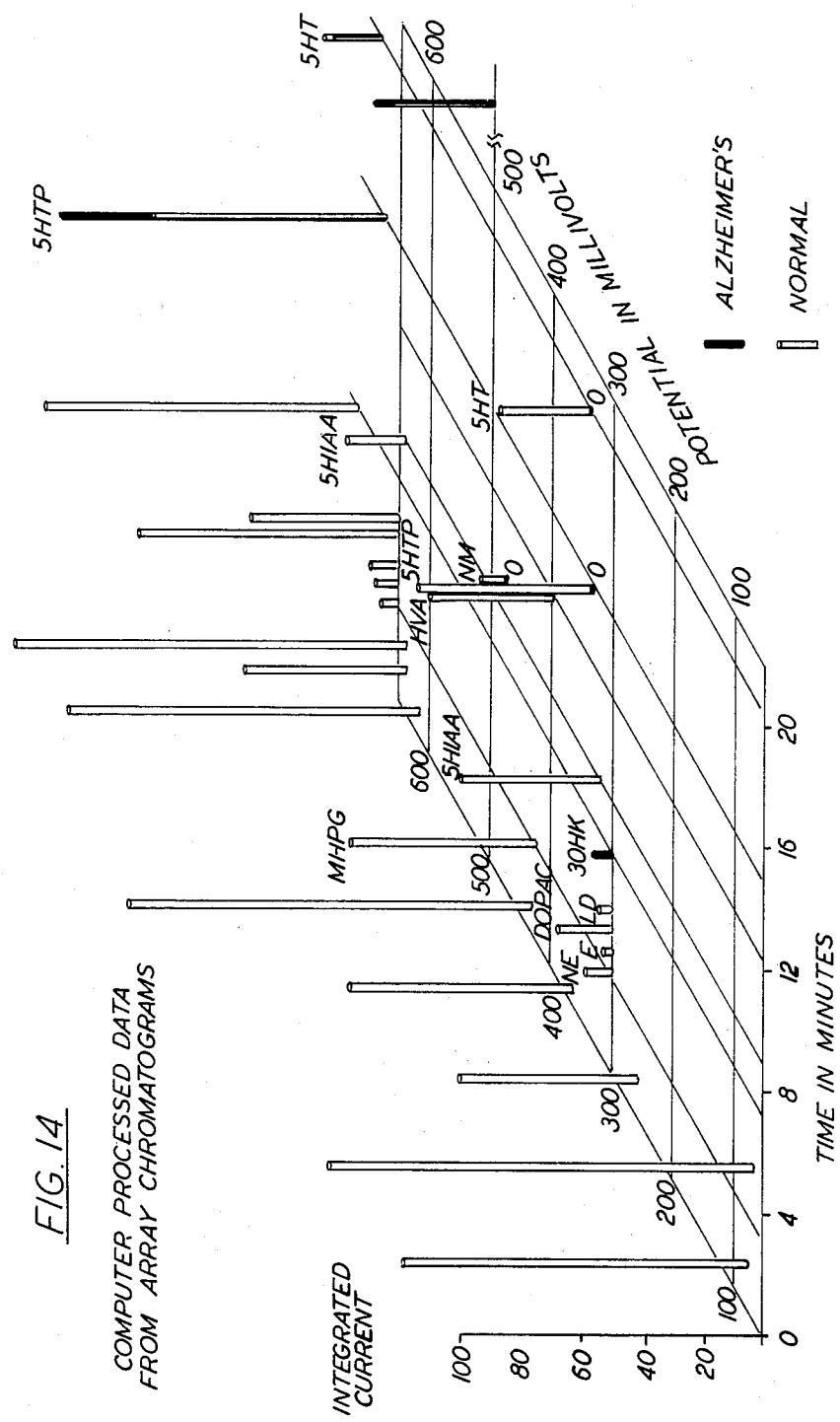
FIG. 14 is a combination of FIGS. 12 and 13 which has been processed by computer to accentuate the differences between the two array chromatograms.

An example of this is shown in FIG. 14. The Figure represents principally the compounds that have been identified as being of substantial or known interest as neurotransmitters. A great number of the other points on the chromatogram have been omitted in FIG. 14 for the sake of clarity. In this representation a typical normal is shown as the light lines on the graph and the points of difference between the normals and the Alzheimer's CSF are the dark lines. As can be seen, there are some additional binary points of difference between the normals and the Alzheimer's. First, as has been discussed, the dominant effect seems to be the occurrence of the 5-hydroxy tryptamine and 5-hydroxy tryptophan, as the partially oxidized form in the Alzheimer's samples. In the Alzheimer's samples no peak was observed at the point identified as normetanephrine in normals and a small but resolvable peak was seen in the region identified as 3-hydroxy kynurenine, which represents a different pathway for tryptophan metabolism than the pathway which leads to serotonin and 5-hydroxy tryptophan. In the Alzheimer's samples a late eluting peak was seen in the voltage time region which in a series of other experiments appeared to be associated with the partial oxidation of serotonin.

The invention has been described for analyzing catecholamines. One skilled in the art will recognize, however, that the invention may advantageously be employed for separating and measuring a large number of electroactive organic substances among which are mentioned unsaturated hydrocarbons, azides, triazines and phenothaizines, amino acids, amines and amides, phenols, aromatic OH, quinolines, quinones, imines, olefins, ketones, aldehydes, esters, olefinic esters, ethers, organometallics, diazo compounds, nitro compounds, and halogens. The electrochemical detection system of the present invention also may be advantageously employed for separating and measuring substances such as cyanide, halogens, $SO_2$ and $NO_x$ and complexed heavy metals in biological samples, water or sewage. Electroactive organo metallic compounds in association with macro molecules also can be separated and measured using the electrochemical apparatus of the present invention.

Still other changes and advantages will be obvious to one skilled in the art.

I claim:

1. An electrochemical detection apparatus for electrochemically testing a sample containing reversible and irreversible electrochemically active materials in solution, said apparatus comprising:
   at least three coulometric electrochemical flow cell, each of said cells having therein at least one working electrode, at least one counter electrode and at least one reference electrode, said plurality of electrochemical cells being arranged in series and defining collectively at least one flow channel for said sample solution;
   means for connecting each said reference electrode to a reference potential;
   means connecting each said counter electrode to a counter potential; and
   means connecting each said working electrode to a working potential, at least two of said cells constituting gate cells, each of said gate cells having means for maintaining its working electrode at a different potential from the other, one of said gate cells being at a potential to oxidize electrochemically active materials in said sample and another of said gate cells being at a potential to reduce electrochemically active materials in said sample
   said remaining cell or cells having means for maintaining its working electrode at a potential to detect and coulometrically measure electrochemically reversible materials in said sample.

2. In an apparatus for analyzing complex mixtures of electrochemically active fluids such as blood, cerebrospinal fluids and the like containing electrochemically irreversible materials and trace quantities of electrochemically reversible materials, comprising a liquid chromatographic column for achieving time spaced separation of the materials eluting from the column and an electrochemical detection apparatus for electrochemically testing a sample containing reversible and irreversible electrochemically active materials in solution, the improvement wherein said detection apparatus comprises at least three coulometric electrochemical flow cells, each of said cells having therein at least one working electrode, at least one counter electrode and at least one reference electrode, said plurality of electrochemical cells being arranged in series and defining collectively at least one flow channel for said sample solution;

means for connecting each said reference electrode to a reference potential;

means connecting each said counter electrode to a counter potential; and means connecting each said working electrodes to a working potential, at least two of said cells constituting gate cells, each of said gate cells having means for maintaining its working electrode at a different potential from the other, one of said gate cells being at a potential to oxidize electrochemically active materials in said sample and another of said gate cells being at a potential to reduce electrochemically active materials in said sample said remaining cell or cells having means for maintaining its working electrode at a potential to detect and coulometrically measure electrochemically reversible materials in said sample.

3. The apparatus of claim 2 wherein said detection apparatus includes at least two measuring cells following said gate cells, the working electrodes of said measuring cells being at different potentials to provide different electrochemical measurements for electrochemically active species passing sequentially through said two measuring cells.

4. The apparatus of claim 3 wherein said two measuring cells operate at progressively varying potentials along said flow path.

5. The apparatus of claim 4 wherein means are provided for displaying said measurements so as to separate said measurements by measuring potential as well as by time of elution.

6. The apparatus of claim 5 wherein the measuring cells are sufficiently close along said channel that time of transit of eluant between measuring cells is insignificant with respect to overall elution times.

7. The apparatus of claim 2 wherein the working electrode in each gate cell has an area equal to at least 50 half times, the area of the working electrode in the detection cell being less than 1/10 that of the preceding gate cell working electrode.

8. In apparatus for analyzing complex mixtures of electrochemically active fluids such as blood, cerebrospinal fluids and the like containing electrochemically irreversible materials and trace quantities of electrochemically materials, comprising a liquid chromatographic column for achieving time spaced separation of the materials eluting from the column and an electrochemical detection apparatus for electrochemically testing a sample containing reversible and irreversible electrochemically active materials in solution, the improvement wherein said detection apparatus comprises at least two gate cells arranged to change the oxidation state of electrochemically reversible and electrochemically irreversible materials and convert at least some of said materials to an electrochemically inactive state at the potential on a following coulometric measuring electrode, at least one additional test cell following said two gate cells, arranged to coulometrically measure electrochemically reversible materials of interest in the eluant at a measuring electrode held at a potential adequate to detect and measure the quantity of said materials of interest.

9. The apparatus of claim 8 wherein said oxidizing gate cell precedes said reducing gate cell.

10. The apparatus of claim 8 wherein said reducing gate cell precedes said oxidizing gate cell.

11. The apparatus of claim 8 wherein said measuring cell reduces said electrochemically reversible species.

12. The apparatus of claim 8 wherein said measuring cell oxidizes said electrochemically reversible species.

13. The method for analyzing complex mixtures of electrochemically active fluids containing electrochemically irreversible materials and trace quantities of electrochemically reversible materials comprising the steps of passing said electrochemically active fluids sequentially through a liquid chromatographic column for achieving time spaced separation of the materials eluting from the column and an electrochemical detection apparatus for electrochemically testing a sample containing reversible and irreversible electrochemically active materials in solution, the detection apparatus comprising at least three coulometric cells arranged in series, maintaining the coulometric electrodes of two of said cells at different potentials to change the oxidation state of electrochemically reversible and electrochemically irreversible materials and convert at least some of said materials to an electrochemically inactive state at the potential maintained on a following coulometric measuring electrode, providing at least one additional test cell following said two gate cells, and coulometrically measuring electrochemically reversible materials of interest in the eluant at a measuring electrode held at a potential adequate to detect and measure the quantity of said materials of interest.

14. The method of claim 13 wherein said detection apparatus includes at least two measuring cells following said gate cells, the working electrodes of said measuring cells being at different potentials to provide different electrochemical measurements for electrochemically active species passing sequentially through said two measuring cells.

15. The method of claim 14 wherein said two measuring cells operate at progressively varying potentials along said flow path.

16. The method of claim 15 including the additional step of displaying said measurements so as to separate said measurements by measuring potential as well as by time of elution.

17. The method of claim 14 wherein the measuring cells are sufficiently close along said channel that time of transit of eluant between measuring cells is insignificant with respect to overall elution times.

18. The method of claim 13 wherein said electrochemically active fluid comprises blood.

19. The method of claim 13 wherein said electrochemically active fluid comprises cerebrospinal fluid.

20. The method for analyzing complex mixtures of electrochemically active fluids containing electrochemically irreversible materials and trace quantities of electrochemically reversible materials comprising the steps of passing said electrochemically active fluids sequentially through a liquid chromatographic column for achieving time spaced separation of the materials eluting from the column and an electrochemical detection apparatus for electrochemically testing a sample containing reversible and irreversible electrochemically active materials in solution, the detection apparatus comprising at least three coulometric cells arranged in series, maintaining the coulometric electrodes of two of said cells at different potentials to change the oxidation state of electrochemically reversible and electrochemically irreversible materials and convert at least some of said materials to an electrochemically inactive state at the potential maintained on a following coulometric measuring electrode, providing at least one additional test cell following said two gate cells and coulometrically measuring electrochemically reversible materials of interest in the eluant at a measuring electrode held at a potential adequate to detect and measure the quantity of said materials of interest, connecting each said working electrodes to a working potential, at least two of said cells constituting gate cells, each of said gate cells having its working electrode at a different potential from the other, one of said gate cells being at a potential to oxidize electrochemically active materials in said sample and another of said gate cells being at a potential to reduce electrochemically active materials in said sample said remaining cell or cells having its working electrode at a potential to detect and coulometrically measure electrochemically reversible materials in said sample.

21. The method of claim 20 wherein said oxidizing gate cell precedes said reducing gate cell.

22. The method of claim 20 wherein said reducing gate cell precedes said oxidizing gate cell.

23. The method of claim 20 wherein said measuring cell reduces said electrochemically reversible species.

24. The method of claim 20 wherein said measuring cell oxidizes said electrochemically reversible species.

25. The method of claim 20 wherein said electrochemically active fluid comprises blood.

26. The method of claim 20 wherein said electrochemically active fluid comprises cerebrospinal fluid.

* * * * *